United States Patent [19]

Graf et al.

[11] Patent Number: 4,663,324

[45] Date of Patent: May 5, 1987

[54] PYRIDAZINONE DERIVATIVES, THEIR PREPARATION AND THEIR USE AS FUNGICIDES

[75] Inventors: Hermann Graf, Mutterstadt; Costin Rentzea, Heidelberg; Winfried Richarz, Stockstadt; Helmut Froehlich; Eberhard Ammermann, both of Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 639,324

[22] Filed: Aug. 10, 1984

[30] Foreign Application Priority Data

Aug. 10, 1983 [DE] Fed. Rep. of Germany ....... 3328770

[51] Int. Cl.$^4$ .................... A01N 43/58; C07D 237/18
[52] U.S. Cl. ..................................... 514/247; 544/240
[58] Field of Search ................ 544/240, 241; 424/250; 514/247

[56] References Cited

U.S. PATENT DOCUMENTS 2,628,181  2/1953  Mowry ............................... 514/247

FOREIGN PATENT DOCUMENTS 1445475  11/1968  Fed. Rep. of Germany .
3143303   5/1983  Fed. Rep. of Germany ...... 544/240
   9344   5/1967  Japan ..................................... 544/240

OTHER PUBLICATIONS

M. Takaya et al., Chem. Abstracts, 87:201567k (1977), Sulfonylpyridazinones.
Chemical Week, Jun. 21, 1972, p. 46.
Chemical Abstract 68, 2906c (1968), K. Kaji.

Primary Examiner—Mary E. Ceperley
Attorney, Agent, or Firm—Keil & Weinkauf

[57] ABSTRACT

Pyridazinone derivatives of the formula I

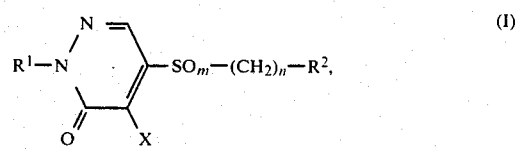

where $R^1$ is hydrogen, unsubstituted or substituted alkyl, cycloalkyl, or unsubstituted or substituted phenyl or is carboxyl, hydroxymethyl or $-CH_2O-COR^3$, where $R^3$ is alkyl, or is $-CH_2O[CH_2CH_2O]_pR^4$, where $R^4$ is alkyl or phenyl and p is 1, 2 or 3, $R^2$ is phenyl, unsubstituted or substituted vinyl or 2-propenyl, X is halogen, m is 1 or 2 and n is 1, 2, 3 or 4, and fungicides containing these compounds.

3 Claims, No Drawings

PYRIDAZINONE DERIVATIVES, THEIR PREPARATION AND THEIR USE AS FUNGICIDES

The present invention relates to novel pyridazinone derivatives, a process for their preparation, fungicides which contain these compounds as active ingredients, and methods of controlling fungi.

It is known that N-trichloromethylthiotetrahydrophthalimide can be used as a fungicide in agriculture, fruit cultivation and horticulture (cf. for example Wegler, Chemie der Pflanzenschutz- und Schädlingsbekampfungsmittel, volume 2, page 109 et seq, Springer Verlag Berlin/Heidelberg/New York, 1970). However, the known agent can only be used before infection, and, when small amounts are applied, its action does not meet practical requirements.

We have found that pyridazinone derivatives of the formula I

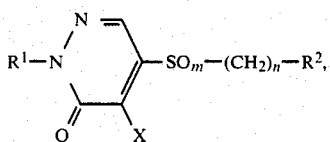

where
R$^1$ is hydrogen or C$_1$-C$_8$-alkyl which is unsubstituted or monosubstituted or polysubstituted by halogen, or is C$_3$-C$_7$-cycloalkyl, or is phenyl which is unsubstituted or monosubstituted or polysubstituted by halogen, C$_1$-C$_4$-alkyl, mono-, di- or trihalo-C$_1$-C$_3$-alkyl, mono-, di- or trihalo-C$_1$-C$_3$-alkoxy, C$_1$-C$_4$-alkoxy, C$_1$-C$_4$-alkylthio, C$_1$-C$_4$-alkylsulfinyl, C$_1$-C$_4$-alkylsulfonyl, C$_1$-C$_4$-alkoxycarbonyl, mono- or di(C$_1$-C$_4$-alkyl)-carbamyl, cyano, thiocyano or nitro, the substituents being identical or different in the case of polysubstitution, or is carboxyl, hydroxymethyl or —CH$_2$O-COR$^3$, where R$^3$ is C$_1$-C$_6$-alkyl, or is —CH$_2$O[CH$_2$CH$_2$O]$_p$R$^4$, where R$^4$ is C$_1$-C$_4$-alkyl or phenyl and p is 1, 2, or 3;

R$^2$ is phenyl which is unsubstituted or monosubstituted or polysubstituted by halogen, C$_1$-C$_4$-alkyl (unsubstituted or monosubstituted or polysubstituted by halogen), C$_1$-C$_4$-alkoxy (unsubstituted or monosubstituted or polysubstituted by halogen), C$_1$-C$_4$-alkylthio, C$_1$-C$_4$-alkylsulfinyl, C$_1$-C$_4$-alkylsulfonyl, mono- or di(C$_1$-C$_4$-alkyl)-carbamyl, cyano, thiocyano or nitro, the substituents being identical or different in the case of polysubstitution, or is vinyl or 2-propenyl;

X is halogen;

m is 1 or 2 and n is 1, 2, 3 or 4, possess good fungicidal activity and are easy to prepare.

In formula I R$^1$ is preferably methyl or phenyl, R$^2$ is preferably phenyl, X is preferably chlorine or bromine, m is preferably two and n is preferably one or two.

The novel pyridazinone derivatives of the formula I can be prepared by a method in which a 4,5-dihalopyridazin-3(2H)-one of the formula II

is reacted with a mercaptan of the formula III

where R$^1$, R$^2$, X and n have the above meanings, in the presence of a base, for example in an organic solvent, and the resulting thio compound IV

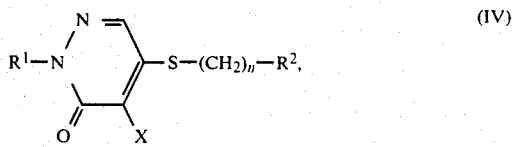

is oxidized, in the presence or absence of an inorganic or organic solvent, to give a compound of the formula I.

Compounds of the type IV are known, but the conventional methods of preparation entail two stages, starting from the dihalo compound II, or give undesirable by-products. Chem. Abstr. 68, (1968), 2906 c describes the preparation of 4-chloro-5-mercapto-2-phenylpyridazin-3(2H)-one (V) starting from 4,5-dichloro-2-phenylpyridazin-3(2H)-one (II, R$^1$=C$_6$H$_5$, X=Cl) and sodium hydrogen sulfide, the product (V) being reacted with benzyl chloride and sodium hydroxide and ammonium hydroxide to give the desired compound 5-benzylthio-4-chloro-2-phenyl-pyridazin-3-(2H)-one.

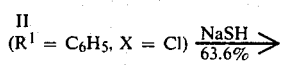

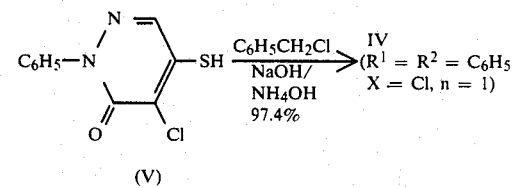

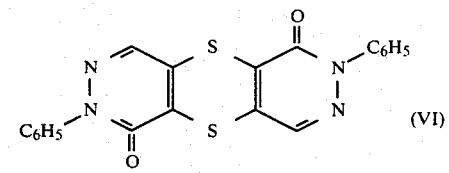

However, the first stage gives 2,7-diphenyl dipyridazo-[4,5-b: 4,5-e]-1,4-dithiine-1,6-dione (VI) as an undesirable by-products (cf. R. N. Castle, K. Kaji and D. Wise, J. Heterocyclic Chem. 3 (1966), 541–543 and K. Kaji, M. Kuzuya and R. N. Castle, Chem. Pharm. Bull. 18, (1970), 147–156).

Another conventional method (cf. R. F. Meyer, J. Heterocyclic Chem. 6, (1969), 407–408) starts from 4,5-dichloro-2-methylpyridazin-3(2H)-one (II, R$^1$=CH$_3$ and X=Cl), and empolys only one stage to give the desired 5-benzylthio-4-chloro-2-methyl-pyridazin-3(2H)-one (IV, R$^1$=CH$_3$, R$^2$=C$_6$H$_5$, X=Cl and n=1), but the yield is only 37%. Furthermore, the S-benzylisothiouronium chloride required is not available commercially and has to be prepared specially.

As our own experiments have shown, there is furthermore the possibility of the undesirable products VII and VIII being formed.

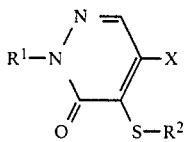

(VII)

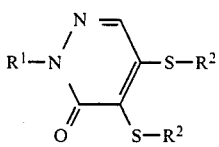

(VIII)

We have found that 5-thiosubstituted pyridazinones of the type IV can be obtained from 4,5-dihalogen-substituted pyridazinones II in one stage without troublesome side reactions.

To do this, a 4,5-dihalogen-substituted pyridazinone of the type II is reacted with a mercaptan III in the presence of a base and in a non-nucleophilic solvent at from −40° C. to +100° C. preferably from −20° C. to +50° C.

Preferred bases are amines, such as trimethylamine, triethylamine, triisobutylamine, dimethylethylamine, ethyldiisopropylamine, N,N-dimethylaniline, N,N-diethylaniline or 2-(diethylamino)-ethanol.

Examples of solvents are alcohols, such as isopropanol, sec.-butanol, tert.-butanol, sec.-isoamyl alcohol and tert.-amyl alcohol.

The oxidation of the 5-thiosubstituted pyridazinones IV to 5-sulfinyl-substituted (I, m=1) or 5-sulfonyl-substituted (I, m=2) pyridazinones can be carried out using, for example, peroxides, e.g. hydrogen peroxide or tert.-butyl hydroperoxide, per-acids, e.g. performic acid, peracetic acid, perbenzoic acid or m-chloroperbenzoic acid, periodates, e.g. sodium periodate or potassium periodate, permangenates, e.g. sodium permanganate or potassium permanganate, tert.-butyl hypochlorite or iodobenzene dichloride.

Suitable solvents are water, carboxylic acids, e.g. formic, acetic or propionic acid, and halohydrocarbons, e.g. dichloromethane, chloroform, 1,2-dichloroethane, 1,1,1-trichloroethane or 1,1,2,2-tetrachloroethane.

The oxidation is carried out at, for example, from −20° to +120° C., preferably from −10° to 80° C. Depending on the number of equivalents of oxidizing agent used per equivalent of the compound IV, the corresponding sulfoxides (I, m=1) or sulfones (I, m=2) can be obtained.

The preparation of the required 4,5-dihalogen-substituted pyridazinones II is known (cf. K. Dury, Angew. Chem. 77 (1985), 282–290), as is the preparation of the necessary mercaptans (cf. J. L. Wardell in S. Patai, The Chemistry of the Thiol Group, vol 1, pages 179–211, Wiley and Sons New York 1974).

The Examples which follow illustrate the invention without restricting it.

METHOD 1

Preparation of 5-benzylthio-4-chloro-2-phenylpyridazin-3(2H)-one using sodium methylate as a base.

5.4 g (100 millimoles) of sodium methylate in 250 ml of dry methanol are initially taken and cooled to 0° C., 12.4 g (100 millimoles) of benzyl mercaptan are slowly added dropwise and 24.1 g (100 millimoles) of 4,5-dichloro-2-phenylpyridazin-3(2H)-one are then added at the same temperature. The mixture is then allowed to reach room temperature (20° C.) slowly, and stirring is continued for 24 hours, for the final 5 hours at 60° C. The reaction solution is evaporated down, water is added to the residue, and the mixture is brought to pH 3 with hydrochloric acid and is extracted with dichloromethane. The organic phase is washed with dilute NaHCO$_3$ solution, dried over MgSO$_4$ and evaporated down. Stripping off the solvent gives 29.1 g of crude material, which is recrystallized from ethanol. A residue (5.0 g) which is insoluble in ethanol is filtered off and dried, after which it has a melting point of 158°–160° C. (literature value: 163°–164° C.; cf. R. N. Castle and K. Kaji, J. Heterocyclic Chem. 2 (1965), 463–472). It is identical to 4,5-bis(benzylthio)-2-phenyl-pyridazin-3(2H)-one (VIII, R$^1$=C$_6$H$_5$ and R$^2$=CH$_2$C$_6$H$_5$). The material (21.2 g) which crystallises out from the filtrate exhibits two melting points (115°–119° C. and 135°–140° C.), gives two closely adjacent spots in the thin-layer chromatogram, and consists of 5-benzylthio-4-chloropyridazin-3(2H)-one (IV, R$^1$=R$^2$=C$_6$H$_5$, X=Cl and n=1) and the position isomer 4-benzylthio-5-chloro-2-phenyl-pyridazin-3(2H)-one (VII, R$^1$=C$_6$H$_5$, R$^2$=CH$_2$C$_6$H$_5$, X=Cl) in a ratio of about 1:1 (NMR analysis). The 5-benzylthio derivative can be separated from this mixture by column chromatography.

METHOD 2

Preparation of 5-benzylthio-4-chloro-2-phenylpyridazin-3(2H)-one using triethylamine as the base.

24.1 g (100 millimoles) of 4,5-dichloro-2-phenylpyridazin-3(2H)-one are suspended in 150 ml of isopropanol at −20° C., and a cooled mixture of 12.4 g (100 millimoles) of benzyl mercaptan, 10.1 g (100 millimoles) of triethylamine and 150 ml of isopropanol is added dropwise. Stirring is then continued for 2 hours at −10° C., overnight at room temperature and then for 2.5 hours at 40° C. The mixture is cooled, and the resulting precipitate is filtered off under suction, washed with isopropanol and water and recrystallized from toluene. The material obtained (19.5 g, 59%) is found to be pure by thin-layer chromatography, and has a melting point of 139°–140° C.

METHOD 3

Preparation of 5-(4-chlorobenzylthio)-4-chloro-2-phenylpyridazin-3(2H)-one.

The reaction of 15.8 g (100 millimoles) of 4-chlorobenzyl mercaptan with 24.1 g (100 millimoles) of 4,5-dichloro-2-phenylpyridazin-3(2H)-one and 10.1 g (100 millimoles) of triethylamine is carried out as described in Method 2 and gives 30.5 g (84%) of a material which is found to be pure by thin-layer chromatography and has a melting point of 154°–155° C.

METHOD 4

Preparation of 5-benzylthio-4-chloro-2-methyl-pyridazin-3(2H)-one.

35.8 g (200 millimoles) of 4,5-dichloro-2-methyl-pyridazin-3(2H)-one are suspended in 300 ml of isopropanol and the suspension is colled to −20° C. A solution of 24.8 g (200 millimoles) of benzyl mercaptan and 20.2 g (200 millimoles) of triethylamine in 200 ml of isopropanol is added dropwise at this temperature, after which stirring is continued for 1 hour at −10° C. and overnight at room temperature. The resulting precipitate is filtered off under suction, washed with isopropanol and water and dried under reduced pressure to give 31.7 g (60%) of a product of melting point 102°–104° C.

METHOD 5

Preparation of 5-benzylthio-4-bromo-2-methylpyridazin-3(2H) one 40.2 g (150 millimoles) of 4,5-dibromo-2-methylpyridazin-3(2H)-one are reacted with 18.6 g (150 millimoles) of benzyl mercaptan and 15.1 g (150 millimoles) of triethylamine in a total of 400 ml of isopropanol by the procedure described in Method 4. 20.0 g (43%) of a product of melting point 118°–121° C. are obtained.

EXAMPLE 1

Preparation of 5-benzylsulfonyl-4-chloro-2-phenylpyridazin-3(2H)-one 9.8 g (30 millimoles) of 5-benzylthio-4-chloro-2-phenylpyridazin-3(2H)-one from Method 2 were dissolved in 100 ml of glacial acetic acid at 60° C. and 25 ml of 30% strength hydrogen peroxide were added dropwise. The mixture was kept at 65° C. for 3 hours and then allowed to cool, and the resulting precipitate was filtered off under suction, washed peroxide-free with water and dried under reduced pressure to give 7.9 g (73%) of a product of melting point 154°–156° C. (active ingredient no. 61 b).

EXAMPLE 2

Preparation of 5-benzylsulfinyl-4-chloro-2-methylpyridazin-3(2H)-one 16.0 g (60.0 millimoles) of 5-benzylthio-4-chloro-2-methylpyridazin-3(2H)-one from Method 4 were dissolved in 200 ml of dichloromethane, the solution was cooled to −20° C. and a solution of 11.4 g (66.1 millimoles) of m-chloroperbenzoic acid in dichloromethane was added dropwise. Stirring was continued for 1 hour at −10° C., and then overnight at room temperature. The reaction solution was washed three times with saturated NaHCO$_3$ solution and once with water, dried and evaporated down, and the residue was triturated with diethyl ether and then filtered off under suction to give 13.1 g (77%) of a product of melting point 129°–131° C. (active ingredient no. 2 a).

The following pyridazinone derivatives can be prepared by the stated methods:

TABLE 1

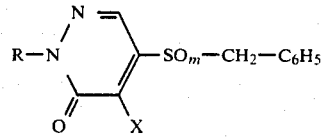

| No. | R | X | m = 0 (precursor) | m = 1 a | m = 2 b |
|---|---|---|---|---|---|
| 1 | H | Cl | 183–187 | 212 (decomp.) | 236 (decomp.) |
| 2 | CH$_3$ | Cl | 102–104 | 129–131 | 186–188 |
| 3 | CH$_3$ | Br | 118–121 | 129–132 | 155–157 |
| 4 | C$_2$H$_5$ | Cl | 114–116 | | 117–119 |
| 5 | n-C$_3$H$_7$ | Cl | | | |
| 6 | i-C$_3$H$_7$ | Cl | 106–198 | 75–77 | 130–132 |
| 7 | n-C$_4$H$_9$ | Cl | 88–90 | | 82–84 |
| 8 | i-C$_4$H$_9$ | Cl | | | |
| 9 | t-C$_4$H$_9$ | Cl | 72–75 | | 142–146 |
| 10 | (H$_3$C)$_3$C—CH$_2$ | Cl | 108–110 | 115–118 | 107–109 |
| 11 | (C$_2$H$_5$)(H$_3$C)CH | Cl | 107–109 | | 78–81 |
| 12 | (H$_3$C)$_2$CHCH$_2$(H$_3$C)CH | Cl | 88–90 | 66–69 | 70–72 |
| 13 | cyclo-C$_6$H$_{11}$ | Cl | 167–170 | 156–159 | 175–179 |
| 14 | HOCH$_2$ | Cl | 164–166 | | |
| 15 | HOCH$_2$ | Br | | | |
| 16 | HO$_2$C | Cl | | | 238 (decomp.) |
| 17 | HO$_2$C | Br | | | |
| 18 | H$_3$CCOOCH$_2$ | Cl | 120–122 | | 112–114 |
| 19 | H$_3$CO(CH$_2$)$_2$OCH$_2$ | Cl | | | |
| 20 | H$_5$C$_6$O(CH$_2$)$_2$OCH$_2$ | Cl | | | |
| 21 | H$_5$C$_6$O(CH$_2$)$_2$O(CH$_2$)$_2$OCH$_2$ | | | | |
| 22 | ClCH$_2$ | Cl | | | |
| 23 | F$_3$CCH$_2$ | Cl | 113–115 | | 139–141 |
| 24 | Cl$_3$CCH$_2$ | Cl | | | |
| 25 | 2-Cl—C$_6$H$_4$ | Cl | | | |
| 26 | 3-Cl—C$_6$H$_4$ | Cl | 160–162 | 110–116 | 165–167 |
| 27 | 4-Cl—C$_6$H$_4$ | Cl | | | |
| 28 | 3,5-Cl$_2$—C$_6$H$_3$ | Cl | 129–131 | 151–153 | 181–184 |
| 29 | 2,4,6-Cl$_3$—C$_6$H$_2$ | Cl | 171–174 | 149–152 | 177–179 |
| 30 | 3-Br—C$_6$H$_4$ | Cl | | | |
| 31 | 4-Br—C$_6$H$_4$ | Cl | 182–184 | | 171–174 |
| 32 | 3-(F$_3$O)—C$_6$H$_4$ | Cl | 133–135 | 116–117 | 179–181 |
| 33 | 3-(F$_3$C)—C$_6$H$_4$ | Br | 165–167 | 89–93 | 164–166 |
| 34 | 4-(F$_3$C)—C$_6$H$_4$ | Cl | | | |
| 35 | 4-(F$_3$C)—C$_6$H$_4$ | Br | | | |
| 36 | 3-(F$_3$CO)—C$_6$H$_4$ | Cl | | | |
| 37 | 4-(F$_3$CO)—C$_6$H$_4$ | Cl | | | |
| 38 | 3-(F$_2$HCO)—C$_6$H$_4$ | Cl | | | |
| 39 | 3-(F$_2$HCO)—C$_6$H$_4$ | Br | 133–135 | | 118–122 |
| 40 | 4-(F$_2$CHCF$_2$O)—C$_6$H$_4$ | Cl | | | |
| 41 | 4-(F$_2$CHCF$_2$O)—C$_6$H$_4$ | Br | 154–156 | 172–174 | 207–211 |

TABLE 1-continued

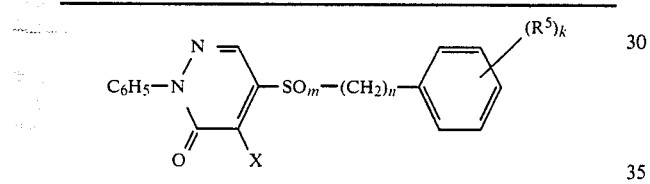

| No. | R | X | m = 0 (precursor) | m = 1 a | m = 2 b |
|---|---|---|---|---|---|
| 42 | 3-($H_3CO$)—$C_6H_4$ | Cl | | | |
| 43 | 4-($H_3CO$)—$C_6H_4$ | Cl | | | |
| 44 | 4-($H_3CS$)—$C_6H_4$ | Cl | | | |
| 45 | 4-($H_3CSO_2$)—$C_6H_4$ | Cl | | | |
| 46 | 2-($H_3C$)—$C_6H_4$ | Cl | | | |
| 47 | 3-($H_3C$)—$C_6H_4$ | Cl | | | |
| 48 | 4-($H_3C$)—$C_6H_4$ | Cl | | | |
| 49 | 4-($H_3COOC$)—$C_6H_4$ | Cl | | | |
| 50 | 4-($H_3C)_2NOC$—$C_6H_4$ | Cl | | | |
| 51 | 2-($O_2N$)—$C_6H_4$ | Cl | | | |
| 52 | 2-($O_2N$)—$C_6H_4$ | Cl | | | |
| 53 | 4-($O_2N$)—$C_6H_4$ | Cl | 208–212 | | 180–183 |
| 54 | 4-($O_2N$)—$C_6H_4$ | Br | | | |
| 55 | 2,4-($O_2N)_2$—$C_6H_3$ | Cl | 172–175 | | 169–172 |
| 56 | 2,4-($O_2N)_2$—$C_6H_3$ | Br | | | |
| 57 | 3-(NC)—$C_6H_4$ | Cl | | | |
| 58 | 3-(NC)—$C_6H_4$ | Cl | | | |
| 59 | 4-(NC)—$C_6H_4$ | Cl | | | |
| 60 | 4-(NCS)—$C_6H_4$ | Cl | | | |

TABLE 2

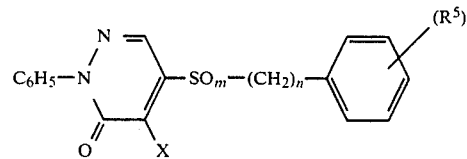

| | | | | M.p. (°C.) | | |
|---|---|---|---|---|---|---|
| No. | $(R^5)_k$ | n | X | m = 0 (precursor) | m = 1 a | m = 2 b |
| 61 | H | 1 | Cl | 139–140 | | 154–156 |
| 62 | H | 1 | Br | 128–131 | 104–106 | 182–183 |
| 63 | H | 2 | Cl | 94–96 | | 130–132 |
| 64 | H | 3 | Cl | 94–96 | | 127–130 |
| 65 | 2-($H_3C$) | 1 | Cl | 164–166 | | 158–160 |
| 66 | 3-($H_3C$) | 1 | Cl | 128–130 | | 148–150 |
| 67 | 4-($H_3C$) | 1 | Cl | 135–137 | 133–135 | 176–178 |
| 68 | 4-($H_3C$) | 1 | Br | | | |
| 69 | 3-(n-$C_3H_7$) | 1 | Cl | | | |
| 70 | 4-(n-$C_3H_7$) | 1 | Cl | | | |
| 71 | 3-(i-$C_3H_7$) | 1 | Cl | | | |
| 72 | 4-(i-$C_3H_7$) | 1 | Cl | 140–142 | 103–106 | 170–173 |
| 73 | 4-(n-$C_4H_9$) | 1 | Cl | | | |
| 74 | 4-(i-$C_4H_9$) | 1 | Cl | | | |
| 75 | 4-(t-$C_4H_9$) | 1 | Cl | 184–186 | 157–160 | 178–180 |
| 76 | 2-F | 1 | Cl | | | |
| 77 | 3-F | 1 | Cl | 140–143 | | 189–190 |
| 78 | 4-F | 1 | Cl | 140–143 | 166–168 | 207–210 |
| 79 | 2-Cl | 1 | Cl | 162–164 | | 173–176 |
| 80 | 3-Cl | 1 | Cl | 148–151 | | 176–178 |
| 81 | 4-Cl | 1 | Cl | 154–155 | | 222–225 |
| 82 | 3,4-$Cl_2$ | 1 | Cl | 170–172 | 193–196 | 218–220 (decomp.) |
| 83 | 3,5-$Cl_2$ | 1 | Cl | | | |
| 84 | 2,4-$Cl_2$ | 1 | Cl | | | |
| 85 | 2,6-$Cl_2$ | 1 | Cl | | | |
| 86 | 3-Br | 1 | Cl | | | |
| 87 | 4-Br | 1 | Cl | | | |
| 88 | 3-$H_3CO$ | 1 | Cl | 132–134 | | 162–163 |
| 89 | 4-$H_3CO$ | 1 | Cl | 212–214 | | 166–168 |
| 90 | 3-CN | 1 | Cl | 183–186 | | 187–189 |
| 91 | 4-CN | 1 | Cl | 190–192 | | 222 (decomp.) |
| 92 | 2-$NO_2$ | 1 | Cl | | | |
| 93 | 3-$NO_2$ | 1 | Cl | 176–177 | | 186–189 |
| 94 | 4-$NO_2$ | 1 | Cl | 175–177 | | more than 240 |
| 95 | 3,5-$(NO_2)_2$ | 1 | Cl | | | |
| 96 | 4-$H_3CS$ | 1 | Cl | | | |
| 97 | 4-$H_3CSO_2$ | 1 | Cl | | | |
| 98 | 4-($H_3C)_2N(OC)$ | 1 | Cl | | | |
| 99 | 4-NCS— | 1 | Cl | | | |

TABLE 3

$H_5C_6-N$...$SO_m-CH_2-R^2$

| No. | $R^2$ | X | m = 0 (precursor) | m = 1 a | m = 2 b |
|---|---|---|---|---|---|
| 100 | $H_2C{=}CH$ | Cl | | | |
| 101 | $H_2C{=}CH$ | Br | | | |
| 102 | $H_2C{=}C(CH_3)$ | Cl | | | |
| 103 | $H_2C{=}C(CH_3)$ | Br | | | |

TABLE 4

$(R^6)_{kl}$ — [pyridazinone with SO$_m$—(CH$_2$)$_n$ linker to phenyl bearing $(R^5)_k$, with substituent X]

| No. | (R⁶)ₗ | (R⁵)ₖ | n | X | M.p. (°C.) m=0 (precursor) | m=1 a | m=2 b |
|---|---|---|---|---|---|---|---|
| 104 | H | 3-F | 1 | Cl | | | |
| 105 | H | 4-F | 1 | Cl | | | |
| 106 | H₃C | 3-F | 1 | Cl | | | |
| 107 | H₃C | 4-F | 1 | Cl | | | |
| 108 | H₃C | 4-F | 2 | Cl | | | |
| 109 | H₃C | 4-F | 1 | Br | | | |
| 110 | H₃C | 3-(H₃CO) | 1 | Cl | | | |
| 111 | H₃C | 4-(H₃CO) | 1 | Cl | | | |
| 112 | H₃C | 4-(H₃CO) | 1 | Br | | | |
| 113 | H₃C | 3-H₃C | 1 | Cl | | | |
| 114 | H₃C | 4-H₃C | 1 | Cl | | | |
| 115 | H₃C | 3,4-(H₃C)₂ | 1 | Cl | | | |
| 116 | C₆H₅ | 3-F | 1 | Cl | | | |
| 117 | C₆H₅ | 4-F | 1 | Cl | | | |
| 118 | C₆H₅ | 4-F | 2 | Cl | | | |
| 119 | C₆H₅ | 4-F | 1 | Br | | | |
| 120 | 4-(O₂N)—C₆H₄ | 3-F | 1 | Cl | | | |
| 121 | 4-(O₂N)—C₆H₄ | 4-F | 1 | Cl | | | |
| 122 | HOCH₂ | 3-F | 1 | Cl | | | |
| 123 | HOCH₂ | 4-F | 1 | Cl | | | |
| 124 | H₅C₆O(CH₂)₂OCH₂ | 3-F | 1 | Cl | | | |
| 125 | H₅C₆O(CH₂)₂OCH₂ | 4-F | 1 | Cl | | | |

The novel active ingredients have a strong fungitoxic action on phytopathogenic fungi. They are particularly suitable for preventing and curing plant diseases caused by microorganisms such as *Phytophthora infestans, Botrytis cinerea, Plasmopara viticola, Monilia fructigena, Alternaria solani, Sclerotinia sclerotiorum, Pyricularia oryzae, Pellicularia filamentosa,* and *Sclerotinia cinerea.*

The active ingredients can simultaneously suppress the growth of two or more of the said fungi, and are well tolerated by plants. Some of the active ingredients have curative properties, i.e., the agents may be applied after the plants have been infected by the pathogen, and success is still ensured.

The fungicidal agents contain from 0.1 to 95, and preferably from 0.5 to 90, wt % of active ingredient. Application rates depend on the type of effect desired, and range from 0.1 to 5 kg/ha.

The active ingredients may also be mixed and applied with other active ingredients, e.g., herbicides, insecticides, growth regulators, other fungicides and fertilizers. When mixed with other fungicides, the spectrum of fungicidal action is in many cases increased. With a number of these fungicidal mixtures, synergistic effects also occur, i.e., the effectiveness of the combination product is greater than the combined effects of the individual components.

Examples of fungicides which may be combined with the active ingredients according to the invention are as follows:

sulfur dithiocarbamates and derivatives thereof, such as
ferric dimethyldithiocarbamate
zinc dimethyldithiocarbamate
manganese ethylenebisdithiocarbamate
zinc ethylenebisthiocarbamate
tetramethylthiuram disulfide
manganese-zinc ethylenediamine-bisdithiocarbamate
zinc-(N,N'-propylene-bisdithiocarbamate)
ammonia complex of zinc-(N,N'-ethylene)bisdithiocarbamate and
N,N'-polyethylene-bis-(thiocarbamoyl)-disulfide ammonia complex of zinc-(N,N'-propylene-bisdithiocarbamate) and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate
heterocyclic structures, such as
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylphthalimide
N-dichlorofluoromethylthio-N',N'-dimethyl-N-phenylsulfuric acid diamide
5-ethoxy-3-trichloromethyl-1,2,3-thiadiazole
2-thiocyanomethylthiobenzthiazole
1,4-dichloro-2,5-dimethoxybenzole
4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiin
2,3-dihydro-5-carboxanilido-6-methyl-1,4-oxathiin-4,4-dioxide
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichloroethane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazolylurea 1-(4-chlorophenoxy)-3,3-dimethyl-1-(1H-1,2,4-
   triazol-1-yl)-2-butanone
1-(4-chlorophenoxy)-3,3-dimethyl-1-(1H-1,2,4-
   triazol-1-yl)-2-butanol
alpha-(2-chlorophenyl)-alpha-(4-chlorophenyl)-5-
   pyrimidinemethanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene
and various fungicides, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-
   alanate methyl D,L-N-(2,6-dimethylphenyl)-N-(2-methoxyacetyl)-alanate
N-(2,6-dimethylphenyl)-N-chloroacetyl-D,L-2-
   aminobutyrolacetone
methyl     DL-N-(2,6-dimethylphenyl)-N-(phenylacetyl)-alanate
5-methyl-5-vinyl-3-(3,5-dichlorophenyl)-2,4-dioxo-
   1,3-oxazolidine
3-(3,5-dichlorophenyl)-5-methyl-5-methoxymethyl-
   1,3-oxazolidin-2,4-dione
3-(3,5-dichlorophenyl)-1-isopropyl-carbamoylhydantoin
N-(3,5-dichlorophenyl)-1,2-dimethyl-cyclopropane-
   1,2-dicarboximide.

The novel active ingredients are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the novel active ingredients as possible.

For the preparation of solutions, emulsions, pastes and oil dispersions to be used direct or after emulsification in water, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc. and strongly polar solvents such as dimethylformamide, dimethyl sulfoxide, and N-methylpyrrolidone, and water.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether, alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Examples of crop protection agent formulations are given below.

I. 90 parts by weight of the compound of Example 1 is mixed with 100 parts by weight of N-methyl-alpha-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of the compound of Example 1 is dissolved in a mixture consisting of 30 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of the compound of Example 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 20 parts by weight of the compound of Example 1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in water, a spray liquor is obtained.

VI. 5 parts by weight of the compound of Example 2 is intimately mixed with 95 parts by weight of particulate kaolin. A dust is obtained containing 5% by weight of the active ingredient.

VII. 30 parts by weight of the compound of Example 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of the compound of Example 2 is intimately mixed with 30 parts of the sodium salt of a phenolsulfonic acid-urea-formaldehyde condensate, 2 parts of silica gel and 48 parts of water to give a stable aqueous dispersion.

IX. 20 parts of the compound of Example 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The following experiments demonstrate the biological action of the novel compounds. The agent used for comparison purposes is in all instances the prior art compound N-trichloromethylthiotetrahydrophthalimide (Chem. Week, June 21, 1972, p. 46), which is especially suitable for combatting Botrytis.

EXAMPLE 1

Action on Botrytis cinerea in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus Botrytis cinerea, and placed at 22° to 24° C. in a chamber of high humidity. After 5 days, the disease had spread to such a great extent on the untreated plants that the necroses covered the major portion of the leaves.

The results of this experiment show that novel active ingredients 2a, 2b, 3b, 4b, 6b, 9b, 10b, 11b, 16b, 61b, 62b and 63b, applied for example as 0.05% spray liquors, have a better fungicidal action (e.g., 97%) than the comparative agent (70%).

Experiment 2

Action of Phytophthora infestans in tomatoes

Leaves of potted tomatoes of the "Grosse Fleischtomate" variety were sprayed with aqueous liquors containing (dry basis A) 80% of active ingredient and 20% of emulsifier. After the sprayed-on layer had dried, the leaves were infected with a zoospore suspension of Phytophthora infestans. The plants were then placed for 5 days in a steam-saturated chamber kept at 16° to 18° C. After this period, the disease had spread on the untreated control plants to such an extent that the fungicidal action of the compouds was able to be assessed.

The results of this experiment show that active ingredients 1b, 2b, 3b, 4b, 6b, 9b, 10b, 11b, 18b, 61b, 62b, 63b, 67b and 72b, applied for instance as 0.025% spray liquors, have a better fungicidal action (e.g., 97%) than the comparative agent (70%).

Experiment 3

Action on Plasmopara viticola

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 10 days in the greenhouse. Then the leaves were infected with a zoospore suspension of Plasmopara viticola. The plants were first placed for 16 hours in a water vapor-saturated chamber at 25° C. and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

The results of the experiment show that for instance active ingredients 1b, 2b, 3b, 4b, 6a, 6b, 7b, 9b, 10b, 11b, 12b, 13b, 16b, 18b, 23b, 33b, 62b, 64b, 67b, 78b, 89b, and 91b have a good fungicidal action (e.g., 90%).

We claim:

1. A process for combating fungi which cause plant diseases, wherein a fungicidally effective amount of a pyridazone derivative is applied to the fungi, on areas in which the plants to be protected grow, or on the plants or seed threatened by fungus attack, said pyridazone derivative having the formula I $$R^1-N \diagdown \underset{O}{\overset{N}{\diagup}} \diagdown SO_m-(CH_2)_n-R^2, \quad X \qquad (I)$$

wherein
R[1] is phenyl which is unsubstituted or monosubstituted or polysubstituted by halogen, $C_1$–$C_4$-alkyl, mono-, di- or trihalo-$C_1$–$C_3$-alkyl, mono-, di- or trihalo-$C_1$–$C_3$-alkoxy, $C_1$–$C_4$-alkoxy, $C_1$–$C_4$-alkylthio, $C_1$–$C_4$-alkylsulfinyl, $C_1$–$C_4$-alkylsulfonyl, $C_1$–$C_4$-alkoxycarbonyl, mono- or di-($C_1$–$C_4$-alkyl)carbamyl, cyano, thiocyano or nitro, the substituents being identical or different in the case of polysubstitution, or is carboxyl, hydroxymethyl or —$CH_2O$-$COR^3$, where $R^3$ is $C_1$–$C_6$-alkyl, or is —$CH_2O[CH_2CH_2O]_pR^4$, where $R^4$ is $C_1$–$C_4$-alkyl or phenyl and p is 1, 2 or 3; $R^2$ is phenyl which is unsubstituted or monosubstituted or polysubstituted by halogen, $C_1$–$C_4$-alkyl (unsubstituted or monosubstituted to polysubstituted by halogen), $C_1$–$C_4$-alkoxy (unsubstituted or monosubstituted or polysubstituted by halogen), $C_1$–$C_4$-alkylthio, $C_1$–$C_4$-alkylsulfinyl, $C_1$–$C_4$-alkylsulfonyl, mono- or di-($C_1$–$C_4$-alkyl)-carbamyl, cyano, thiocyano or nitro, the substituents being identical or different in the case of polysubstitution, or is vinyl or 2-propenyl; X is halogen;
m is 1 or 2 and
n is 1, 2, 3 or 4.

2. A process for combating fungi as set forth in claim 1, wherein the fungi are one or more of Phytophthora infestans, Botrytis cinerea, Plasmopara viticola, Monilia fructigena, Alternaria sloani, Sclerothinia sclerotiorum,

*Pyricularia oryzae, Pellicularia filamentosa,* and *Sclerotinia cinerea.*
3. The process of claim 1, wherein the pyridazone derivative is
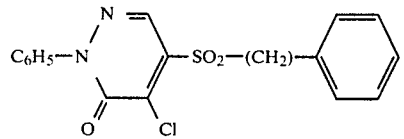
* * * * *